United States Patent [19]

Szonntagh

[11] 4,031,606
[45] June 28, 1977

[54] METHOD OF MAKING A COMBINATION ION RESPONSIVE AND REFERENCE ELECTRODE

[75] Inventor: Eugene L. Szonntagh, Flourtown, Pa.

[73] Assignee: Honeywell Inc., Minneapolis, Minn.

[22] Filed: Feb. 27, 1976

[21] Appl. No.: 661,958

Related U.S. Application Data

[62] Division of Ser. No. 552,284, Feb. 24, 1975, abandoned.

[52] U.S. Cl. .................. 29/570; 29/577; 29/588; 204/195 G
[51] Int. Cl.² ........................... B01J 17/00
[58] Field of Search ............. 29/570, 577, 576 C, 29/588; 204/195 G, 195 F

[56] References Cited
UNITED STATES PATENTS

| | | | |
|---|---|---|---|
| 2,182,376 | 12/1939 | Gray | 29/570 |
| 2,604,517 | 7/1952 | Brennan | 29/570 |
| 2,917,683 | 12/1959 | Brennan | 29/570 |
| 3,282,817 | 11/1966 | Riseman | 204/195 G |
| 3,498,901 | 3/1970 | Metz | 204/195 G |
| 3,853,731 | 12/1974 | Gray | 204/195 G |

*Primary Examiner*—W. Tupman
*Attorney, Agent, or Firm*—Laurence J. Marhoefer; Lockwood D. Burton; Mitchell J. Halista

[57] ABSTRACT

A solid state pH measuring electrode having the pH measuring electrode structure formed by successive layers on an insulating substrate with an outer pH sensitive glass layer being deposited on a supporting solid electrolyte layer by RF sputtering. The reference electrode is similarly formed by depositing an outer layer of glass onto a supporting solid electrolyte layer by RF sputtering with the temperature expansion of the glass and supporting solid electrolyte structure being selected to produce a differential expansion causing random cracking of the glass layer during temperature cycling of the reference electrode. A combination structure is provided wherein the pH measuring electrode and the reference electrode are formed on opposite sides of the same electrically insulating substrate with a thermal compensating element being included in the integrated package.

8 Claims, 3 Drawing Figures

METHOD OF MAKING A COMBINATION ION RESPONSIVE AND REFERENCE ELECTRODE

CROSS REFERENCE TO COPENDING APPLICATION

The present application is a division of application Ser. No. 55,284 filed on Feb. 24, 1975, now abandoned upon the filing of continuation application Ser. No. 666,166 on Mar. 11, 1976 and assigned to the same assignee as the present application.

BACKGROUND OF THE INVENTION

1. Field of the Invention

The present invention relates to ion concentration measuring apparatus. More specifically, the present invention is directed to a solid state ion resposive electrode and reference electrode.

2. Description of the Prior Art

Conventional concentration measuring electrode structures have usually used a glass measuring electrode, a reference electrode and a thermal compensator. For example, various types of special glasses have been used to measure the pH of aqueous solutions. In making these glass electrodes the pH sensitive glass is usually fused to the end of a less expensive glass tube and is subsequently blown into a small bulb of about 2 to 4 mils thick. These "hand-blown" pH glass electrodes are fragile, have very high electrical impedance due to the thickness of the glass and are used for limited temperature ranges mainly because of the internal pressure developed by a liquid electrolyte fill which is subsequently introduced into the interior of the pH measuring electrode to provide an electrically conductive ion source. An example of a typical prior art pH electrode apparatus is shown in U.S. Pat. No. 3,405,048 of D.J. Soltz. These prior art glass electrodes are expensive mainly because of the extensive use of highly skilled manual labor in the construction of the glass envelope and the subsequent filling thereof. A somewhat similar construction is used in the construction of the prior art reference cell which additionally increases the cost of the overall conventional pH measuring system. Despite its disadvantages, the glass electrode has retained its popularity in the field of ion concentration measurement even after attempts to develop a solid state electrode such as that shown in U.S. Pat. No. 3,498,901 of L.T. Metz et al. since the response of the glass electrode is faster than other prior art devices with the glass electrode also having the broadest useful pH range. However, in order to provide a low cost and even more useful ion concentration measuring system it is desirable to produce a low impedance, high reliability and relatively unbreakable pH measuring electrode and reference electrode.

SUMMARY OF THE INVENTION

An object of the present invention is to provide an improved solid state ion reponsive and reference electrode structure.

Another object of the present invention is to provide a method for making a combination ion responsive electrode and reference electrode structure.

In accomplishing these and other objects, there has been provided, in accordance with the present invention, a method for making a combination ion responsive; and reference electrode structure having an insulating substrate supporting an electrically conductive structure overlaid having solid electrolyte layer with a final thin layer ion responsive glass being attached to the solid electrolyte layer by RF sputtering. In the reference electrode, the outer glass layer has a coefficient of thermal expansion different from the solid electrolyte layer while in the ion responsive electrode, the outer pH glass layer is substantially thermally matched to the supporting electrolyte layer.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Figure 1:
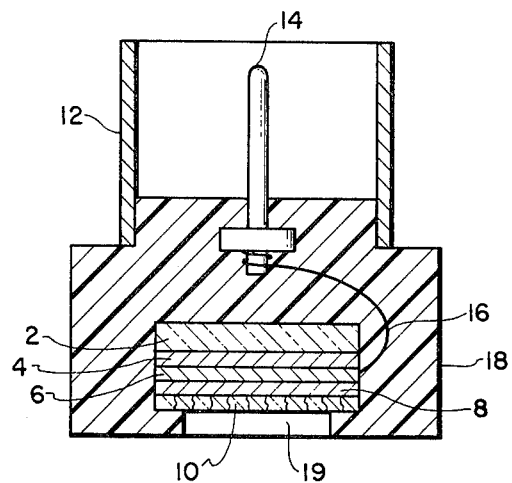
FIG. 1 is a pictorial illustration of a cross-section of a reference electrode embodying the present invention.

Referring to FIG. 1 in more detail, there is shown a pictorial illustration of a cross-section of a reference electrode embodying the present invention. An electrically insulating substrate 2 of an electrically insulating material, e.g., ceramic or glass, has a first layer 4 of chromium (Cr) deposited on one side thereof. A second layer 6 of silver (Ag) is subsequently deposited on he chromium and a third layer 8 of silver chloride (AgCl) is deposited on the silver. An outer layer 10 of a suitable glass is RF sputtered on the exposed surface of the silver chloride layer 8. The glass material for the outer layer 10 is selected to have a coefficient of thermal expansion different from the supporting silver chloride structure 8 whereby a subsequent temperature cycling of the multilayer structure is effective to produce microscopic cracks in the outer glass layer. For example, borosilicate glass has a coefficient approximately one-tenth that of a silver chloride. These cracks provide ion conduction paths to the silver chloride layer from an aqueous solution in which the reference electrode is immersed during pH measurements. A socket shell 12 is arranged to enclose a single contact pin 14. The contact pin is electrically connected by an electrically conducting wire 16 to the silver layer 6 of the multilayer structure. An encapsulating, or potting, compound 18 is subsequently applied to the multi-layer structure, the socket shell 12, the contact pin 14 and the connecting wire 16 to form a moisture-proof barrier and to unite the elements into a rigid package. An open window, or hole, 19 is formed through the potting compound 18 to expose the outer glass layer 10.

Figure 2:
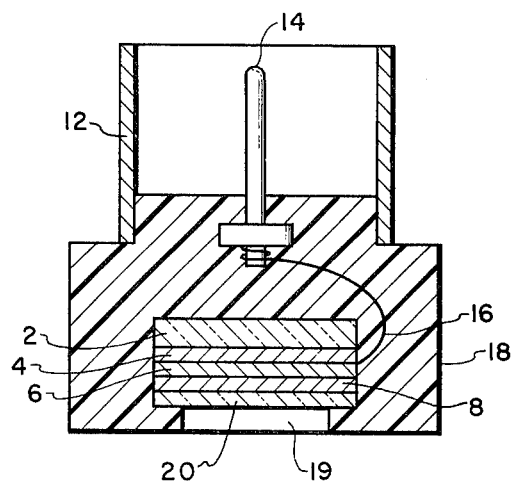
FIG. 2 is a pictorial illustration of a cross-section of an ion concentration measuring electrode embodying the present invention.

In FIG. 2, there is shown a pictorial illustration of an exemplary cross-section of pH measuring electrode embodying the present invention. Similar reference numbers have been used in FIG. 1 and 2 to indicate similar structural elements although the combination of FIG. 2 is directed toward a different device from that shown in FIG. 1. An electrically insulating substrate 2, e.g., glass or ceramic, is used as a support member for a multi-layer structure similar to that used in the reference electrode. Specifically, the glass substrate 2 is first plated with a first layer 4 of chromium which is followed by a second layer 6 of silver and a subsequent third layer 8 of silver chloride. An outer layer 20 of pH sensitive glass is then RF sputtered on the silver chloride layer. The temperature coefficient of the silver chloride and pH glass layer are matched whereby the pH glass will not produce microscopic cracks as during normal temperature cycling, e.g., 0° to 100° C, as in the case of outer glass layer used in the reference electrode previously described. For example, Corning 1990 glass has a coefficient of thermal expansion approximately one-half that of silver chloride. Other pH sensitive glasses can be produced to even more closely match the coefficient of thermal expansion of the silver chloride layer by using glass formulas with the following characteristics: a high coefficient of expansion can be achieved by using oxides such $Li_2O$, $Na_2O$, $K_2O$, $Rb_2O$, $Cs_2O$, BaO and SrO while a low coefficient of expansion can be achieved by using $SiO_2$, $B_2O_3$, $Al_2O_3$, , BeO and $TiO_2$. Thus, the coefficient of thermal expansion of the silver chloride layer or other solid state electrolyte materials such as CuO, AgI, RbI, $RbAg_4I_5$, etc. can be matched to an even closer approximation if either the temperature cycling during the measurement operation or the electrolyte material layer imposes a need for such a match. The thickness of the pH glass is approximately 10 to 10,000 A. A thermal compensator structure may be produced using an insulating substrate with a thermal sensitive element mounted therein and having the same overall configuration as that used for the aforesaid reference and pH electrodes whereby the three elements would be used concurrently as shown in the aforesaid Soltz U.S. Pat. No. 3,405,048.

Figure 3:
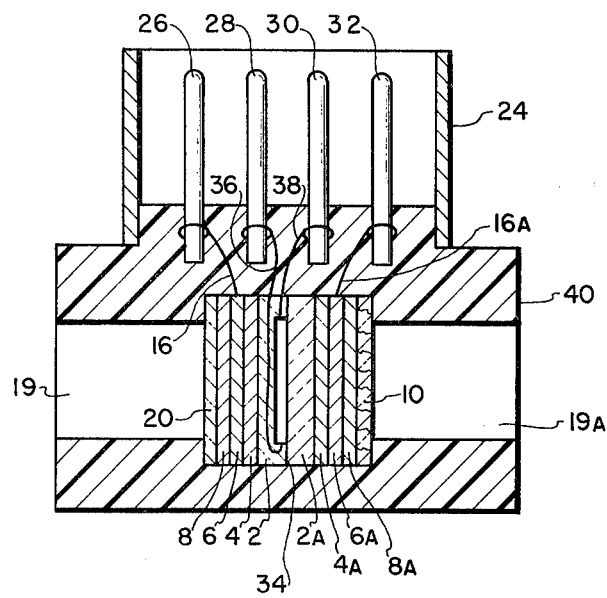
FIG. 3 is a pictorial illustration of a cross-section of a combination ion responsive, reference electrode and thermal compensator embodying the present invention.

In order to further utilize the solid state nature of the electrodes of the present invention, combination structure having the reference electrode, the ion concentration electrode and the thermal compensator integrated therein is shown in FIG. 3. As in the case of FIG. 1 and 2, similar reference numbers have been reused in FIG. 3 for common, or similar, elements of the structure but a capital A reference letter has been added to some repeated reference numbers to indicate similar elements in adjacent sections of the integrated cell structure shown in FIG. 3. Thus, in the case of a pH electrode a first substrate 2 of an electrically insulating material has the first chromium layer 4 followed by the silver layer 6 and the silver chloride layer 8 with an outer layer of the selected mismatched temperature coefficient glass 10 to form the reference electrode portion of the integrated cell. A second electrically insulating substrate 2A has a chromium layer 4A followed by a silver layer 6A and a silver chloride layer 8A with a pH glass outer layer 20. A socket shell 24 which may advantageously be a larger size than the socket shell 12 shown in FIG. 1 and 2 to accommodate an additional number of connector pins is provided adjacent to one side of the aforesaid multilayer structure.

A plurality of electrical connector pins 26, 28, 30 and 32 are located within the connector shell 24. A first one of the pins 26 is connected to the silver layer 6A in the pH measuring electrode section of the integrated multilayer structure by wire 16A. Similarly, the fourth pin 32 is connected by a wire 16 to the silver layer 6 in the reference electrode portion of the integrated multilayer structure. The second and third pins 28 and 30 are connected to a thermal compensator element 34 by separate wires 36 and 38 whereby the thermal compensation element 34 is electrically connected across the second and third pins 28 and 30. The thermal compensator element 34 may be formed in a recess of the second substrate element 2A by any suitable means which can include the same RF sputtering technique used to provide the layers of the pH and reference electrodes structures. Finally, an outer shell, or covering, of a potting compound 40 is provided to enclose the multilayer structure and to secure the pins 26 and 32 while engaging the connector shell 24. A first hole, or window, 19 is provided in the covering 40 to expose the glass layer 10 of the reference electrode while a second opening 19A is provided in the covering 40 to expose the pH glass layer 20 of the pH electrode structure.

MODE OF OPERATION

Since, in the RF sputtering process operation, the operating temperatures are below 200° C, the preparation of the ion responsive electrode structure including the ion responsive glass layer is performed over a much smaller temperature range which further prevents the ion responsive glass from cracking when it is cooled down to room temperature even if the ion responsive glass layer and electrolyte layer do not have an exact temperature coefficient match. Additionally, the thin, i.e., 10,000 A maximum, glass layer will stretch instead of cracking during temperature cycling to enable the overall multilayer structure to withstand temperature cycling over a relatively wide temperature range, e.g., −70° to −200° C. Inherently, the integrated electrode structure has a low impedance due to the thinness of the outer glass layer. Another feature is an extreme ease of replacement whereby the pH electrode, the reference electrode and the thermal compensator can be replaced as a single inexpensive unit. Further, since the delicate glass handling operations required or prior art electrodes have been eliminated, the high manufacturing repeatability of the product and the reduction of manufacturing rejects enhances the low manufacturing costs of either the separate electrodes shown in FIG. 1 and 2 or the combinational electrode structure shown in FIG. 3. Finally, in addition to savings in the amount of materials used for the thin layers of the multilayer structure, additional savings will be effected by the elimination of certain expensive metals which were necessary in previous glass electrodes because of the required glass-to-metal seals, e.g., platinum or other similar thermal property metals.

Accordingly, it may be seen that there has been provided, in accordance with the present invention, a solid state ion responsive and reference electrode structure and method having application in a combination electrode construction.

The embodiments of the invention in which an exclusive property or privilege is claimed are defined as follows:

1. A method of making a combination electrode comprising the steps of depositing a first metallic layer on a first surface area of an insulating substrate, depositing a first solid electrolyte layer on said metallic layer and depositing a pH glass layer on said electrolyte layer, depositing a second metallic layer on a second electrically isolated surface area of said insulating substrate, depositing a second solid electrolyte layer on said second metallic layer, depositing a second glass layer on said second electrolyte layer, said second glass layer having a coefficient of thermal expansion mismatched with respect to a coefficient of thermal expansion of said second electrolyte layer to produce differential expansion therebetween causing cracking of said second glass layer during a predetermined temperature cycle and exposing said electrode to said temperature cycle, said second metallic layer, said second electrolyte layer and said second glass layer being electrically isolated from said first metallic layer, said first electrolyte layer and said pH glass layer.

2. A method of making a combination electrode as set forth in claim 1 wherein said pH glass layer and said second glass layer are deposited by RF sputtering.

3. A method of making a combination electrode as set forth in claim 1 and including the further steps of providing separate electrical connections for said first second metallic layers and encapsulating said substrate, said first and second metallic layers, and a portion of each of said pH glass and said second glass layers while exposing said electrical connections.

4. A method of making a combination electrode as set forth in claim 1 and including the further step of supporting a thermal compensating means on a third electrically isolated surface area of said substrate.

5. A method of making a combination electrode as set forth in claim 4 and including the further steps of providing an electrical connection for said thermal compensating means and encapsulating said thermal compensating means while exposing said electrical connection for said thermal compensating means.

6. A method of making a combination electrode comprising the steps of depositing a first metallic layer on a first surface area of an insulating substrate, depositing a first solid electrolyte layer on said metallic layer and depositing and ion responsive layer on said electrolyte layer, depositing a second metallic layer on a second electrically isolated surface area of said insulating substrate, depositing a second solid electrolyte layer on said second metallic layer and depositing an ion conducting path layer on said second electrolyte layer, said second metallic layer, said second electrolyte layer and said ion conducting path layer being electrically isolated from said first metallic layer, said first electrolyte layer and said ion responsive layer.

7. A method of making a combination electrode as set forth in claim 6 wherein said ion responsive layer is deposited by RF sputtering.

8. A method of making a combination electrode as set forth in claim 6 and including the further steps of providing separate electrical connections for said first and second metallic layers and encapsulating said substrate, said first and second metallic layers, and a portion of each of said ion responsive layer and said ion conducting path layer while exposing said electrical connections.

* * * * *